United States Patent
Linehan (10) Patent No.: US 11,931,496 B2
(45) Date of Patent: Mar. 19, 2024

(54) DISTAL FLOW ARTERIAL CANNULA WITH EXPANDABLE POSITIONING BALLOON

(71) Applicant: CardiacAssist, Inc., Pittsburgh, PA (US)

(72) Inventor: Michael J. Linehan, Pittsburgh, PA (US)

(73) Assignee: CardiacAssist, Inc., Pittsburgh, PA (US)

(*) Notice: Subject to any disclaimer, the term of this patent is extended or adjusted under 35 U.S.C. 154(b) by 542 days.

(21) Appl. No.: 16/803,395

(22) Filed: Feb. 27, 2020

(65) Prior Publication Data

US 2021/0268162 A1    Sep. 2, 2021

(51) Int. Cl.
*A61M 1/16* (2006.01)
*A61M 1/36* (2006.01)
*A61M 25/10* (2013.01)

(52) U.S. Cl.
CPC ........ *A61M 1/1698* (2013.01); *A61M 1/3659* (2014.02); *A61M 25/10* (2013.01); *A61M 2205/3368* (2013.01)

(58) Field of Classification Search
CPC .. A61M 1/1698; A61M 1/3659; A61M 25/10; A61M 2205/3368; A61M 1/16; A61M 1/14; A61M 1/3621; A61M 1/36
See application file for complete search history.

(56) References Cited

U.S. PATENT DOCUMENTS

| | | | |
|---|---|---|---|
| 5,449,342 A | 9/1995 | Hirose et al. | |
| 6,508,777 B1* | 1/2003 | Macoviak | A61M 25/1011 604/9 |
| 8,550,973 B2 | 10/2013 | Magovern et al. | |
| 2002/0188167 A1 | 12/2002 | Viole et al. | |
| 2004/0064091 A1* | 4/2004 | Keren | A61M 1/3659 600/16 |
| 2004/0267358 A1 | 12/2004 | Reitan | |
| 2005/0085761 A1 | 4/2005 | Wang et al. | |
| 2005/0171505 A1* | 8/2005 | Bertolero | A61M 25/1027 604/537 |
| 2009/0187133 A1 | 7/2009 | Matheis et al. | |
| 2014/0275724 A1 | 9/2014 | Wang et al. | |
| 2014/0358071 A1* | 12/2014 | Callaghan | A61M 1/3609 604/27 |

(Continued)

FOREIGN PATENT DOCUMENTS

| | | |
|---|---|---|
| AU | 2016217568 A1 | 7/2017 |
| EP | 1374930 A1 | 1/2004 |

(Continued)

OTHER PUBLICATIONS

International Search Report and Written Opinion dated May 18, 2021 for International Application No. PCT/US2021/019671.

*Primary Examiner* — Jason E Flick
(74) *Attorney, Agent, or Firm* — Seager, Tufte & Wickhem LLP (57) ABSTRACT

A cannula includes a tube having a proximal end, a distal end, and a tubular sidewall extending between the proximal end and the distal end. The cannula further includes an extendable member provided on a portion of the sidewall. The extendable member is configured to extend radially outward from the sidewall. The sidewall defines an aperture located between the proximal end and the distal end of the main tube.

20 Claims, 7 Drawing Sheets

(56) References Cited

U.S. PATENT DOCUMENTS

2018/0228960 A1    8/2018  Marous, III et al.
2020/0360670 A1*  11/2020  Legum ............... A61B 18/1492

FOREIGN PATENT DOCUMENTS

| JP | H5200110 A | 8/1993 |
| JP | 2003088589 A | 3/2003 |
| JP | 2004216138 A | 8/2004 |
| JP | 2005511202 A | 4/2005 |
| WO | 03049647 A1 | 6/2003 |

* cited by examiner

DISTAL FLOW ARTERIAL CANNULA WITH EXPANDABLE POSITIONING BALLOON

BACKGROUND

Field

The present disclosure generally relates to medical cannulas and systems for delivering blood to a patient.

Description of the Related Art

Veno-arterial extracorporeal membrane oxygenation (VA ECMO) is one method for treating right ventricular failure, respiratory failure, and/or cardiac failure percutaneously. A VA ECMO procedure draws blood from the venous circulation and pumps it through an oxygenator and back into the arterial circulation via the femoral artery. VA ECMO bypasses the lungs and the heart completely, elevating arterial pressure and infusing blood into the arterial system with added oxygen and reduced carbon dioxide. In conventional VA ECMO systems, one drainage cannula is placed in the superior vena cava (SVC), interior vena cava (IVC), right atrium region by way of a femoral vein (typically) to drain blood therefrom, and a separate, second return cannula is placed in an artery (typically the femoral artery) to return oxygenated (and cleansed of carbon dioxide) blood at a higher pressure. Insertion of the infusion cannula can cause an obstruction to the blood flow towards the tissue located behind the insertion site. For example, when returning blood to the femoral artery towards the aorta, the blood flow to the foot may be blocked. This may lead to ischemia and in extreme cases loss of limb. Current solutions that allow for a small portion of the infusion flow to be redirected behind the insertion site ("distal flow") are inadequate.

SUMMARY

In the medical and surgical fields, there exists a need for a cannula that facilitates reliable blood flow to prevent ischemia during medical procedures such as VA ECMO. Embodiments of the present disclosure are generally directed to a cannula, a system including a cannula, and a method of extracorporeal blood oxygenation using a cannula.

Embodiments of the present invention are directed to a cannula including a main tube having a proximal end, a distal end, and a tubular sidewall extending between the proximal end and the distal end. The cannula further includes an extendable member provided on a portion of the sidewall. The extendable member is configured to extend radially outward from the sidewall. The sidewall defines an aperture located between the proximal end and the distal end of the main tube.

In some embodiments, the extendable member includes an expandable balloon. The expandable balloon is configured to expand radially outward from the sidewall.

In some embodiments, the cannula further includes an inflator tube in fluid communication with the expandable balloon and extending along at least a portion of the sidewall. The inflator tube is configured to supply liquid or gas to the expandable balloon to cause expansion of the expandable balloon.

In some embodiments, the liquid or gas supplied by the inflator tube is at least one of air, helium, and saline.

In some embodiments, the cannula further includes a lumen defined in the sidewall and in fluid communication with the expandable balloon. The lumen is configured to supply liquid or gas to the expandable balloon to cause expansion of the expandable balloon.

In some embodiments, the expandable balloon includes at least one of a compliant material and a noncompliant material.

In some embodiments, the cannula further includes an absorbent material at least partially filling the expandable balloon. The absorbent material is configured to absorb water from an environment surrounding the expandable balloon to cause expansion of the expandable balloon.

In some embodiments, the absorbent material includes a salt.

In some embodiments, the expandable balloon includes a semipermeable membrane.

In some embodiments, the extendable member includes a flap pivotally connected to the sidewall via a hinge. The flap is configured to rotate about the hinge between a retracted position in which the flap extends substantially parallel to the sidewall and an extended position in which the flap extends radially outward from the sidewall.

In some embodiments, the cannula further includes a mechanical actuator configured to rotate the flap about the hinge between the retracted position and the extended position.

In some embodiments, the flap includes a temperature sensitive material and is configured to rotate to the extended position upon exposure to a body temperature of the patient.

Other embodiments of the present disclosure are directed to an extracorporeal blood oxygenation system. The system includes a drainage cannula configured for insertion into a vasculature of a patient, a blood pump fluidly connected to the drainage cannula and configured to draw blood from the patient via the drainage cannula, an oxygenator in fluid communication with the blood pump and configured to receive blood from the blood pump, and an infusion cannula configured for insertion into the vasculature of the patient. The infusion cannula includes a main tube having a proximal end, a distal end, and a tubular sidewall extending between the proximal end and the distal end. The infusion cannula further includes an extendable member provided on a portion of the sidewall. The extendable member is configured to extend radially outward from the sidewall. The sidewall defines an aperture located between the proximal end and the distal end of the main tube. The proximal end of the infusion cannula is in fluid communication with the oxygenator and configured to return blood from the oxygenator to the vasculature of the patient.

In some embodiments, the extendable member of the infusion cannula includes an expandable balloon. The expandable balloon is configured to expand radially outward from the sidewall of the infusion cannula.

In some embodiments, the extracorporeal blood oxygenation system further comprises a liquid or gas-supplying device for supplying liquid or gas to the infusion cannula. The infusion cannula further includes an inflator tube in fluid communication with the liquid or gas-supplying device and with the expandable balloon. The inflator tube extends along at least a portion of the sidewall. The inflator tube is configured to supply the liquid or gas to the expandable balloon to cause expansion of the expandable balloon.

In some embodiments, the liquid or gas-supplying device is at least one of a syringe and an air pump.

In some embodiments, the infusion cannula further includes an absorbent material at least partially filling the expandable balloon. The absorbent material is configured to absorb water from an environment surrounding the expandable balloon to cause expansion of the expandable balloon.

In some embodiments, the absorbent material includes a salt.

In some embodiments, the expandable balloon includes a semipermeable membrane.

Other embodiments of the present disclosure are directed to a method of extracorporeal blood oxygenation. The method includes inserting a drainage cannula into a first site of the vasculature of a patient and inserting an infusion cannula into a second site of the vasculature of the patient. The infusion cannula includes a main tube having a proximal end, a distal end, and a tubular sidewall extending between the proximal end and the distal end. The infusion cannula further includes an extendable member provided on a portion of the sidewall. The sidewall defines an aperture located between the proximal end and the distal end of the main tube. The method further includes extending the extendable member of the infusion cannula radially outward from the sidewall of the infusion cannula, draining blood through the drainage cannula to a blood pump, pumping, via the blood pump, drained blood through an oxygenator to oxygenate the drained blood, and returning oxygenated blood to the vasculature of the patient via the infusion cannula.

Additional embodiments of the present invention are set forth in the following numbered clauses:

Clause 1. A cannula comprising: a main tube having a proximal end, a distal end, and a tubular sidewall extending between the proximal end and the distal end; and an extendable member provided on a portion of the sidewall, wherein the extendable member is configured to extend radially outward from the sidewall, and wherein the sidewall defines an aperture located between the proximal end and the distal end of the main tube.

Clause 2. The cannula according to clause 1, wherein the extendable member comprises an expandable balloon, and wherein the expandable balloon is configured to expand radially outward from the sidewall.

Clause 3. The cannula according to clause 1 or 2, further comprising an inflator tube in fluid communication with the expandable balloon and extending along at least a portion of the sidewall, wherein the inflator tube is configured to supply liquid or gas to the expandable balloon to cause expansion of the expandable balloon.

Clause 4. The cannula according to any of clauses 1 to 3, wherein the liquid or gas supplied by the inflator tube is at least one of air, helium, and saline.

Clause 5. The cannula according to any of clauses 1 to 4, further comprising a lumen defined in the sidewall and in fluid communication with the expandable balloon, wherein the lumen is configured to supply liquid or gas to the expandable balloon to cause expansion of the expandable balloon.

Clause 6. The cannula according to any of clauses 1 to 5, wherein the expandable balloon comprises at least one of a compliant material and a noncompliant material.

Clause 7. The cannula according to any of clauses 1 to 6, further comprising an absorbent material at least partially filling the expandable balloon, wherein the absorbent material is configured to absorb water from an environment surrounding the expandable balloon to cause expansion of the expandable balloon.

Clause 8. The cannula according to any of clauses 1 to 7, wherein the absorbent material comprises a salt.

Clause 9. The cannula according to any of clauses 1 to 8, wherein the expandable balloon comprises a semipermeable membrane.

Clause 10. The cannula according to any of clauses 1 to 9, wherein the extendable member comprises a flap pivotally connected to the sidewall via a hinge, wherein the flap is configured to rotate about the hinge between a retracted position in which the flap extends substantially parallel to the sidewall and an extended position in which the flap extends radially outward from the sidewall.

Clause 11. The cannula according to any of clauses 1 to 10, further comprising a mechanical actuator configured to rotate the flap about the hinge between the retracted position and the extended position.

Clause 12. The cannula according to any of clauses 1 to 11, wherein the flap comprises a temperature sensitive material and is configured to rotate to the extended position upon exposure to a body temperature of the patient.

Clause 13. An extracorporeal blood oxygenation system comprising: a drainage cannula configured for insertion into a vasculature of a patient; a blood pump fluidly connected to the drainage cannula and configured to draw blood from the patient via the drainage cannula; an oxygenator in fluid communication with the blood pump and configured to receive blood from the blood pump; an infusion cannula configured for insertion into the vasculature of the patient, the infusion cannula comprising: a main tube having a proximal end, a distal end, and a tubular sidewall extending between the proximal end and the distal end; and an extendable member provided on a portion of the sidewall, wherein the extendable member is configured to extend radially outward from the sidewall, wherein the sidewall defines an aperture located between the proximal end and the distal end of the main tube, wherein the proximal end of the infusion cannula is in fluid communication with the oxygenator and configured to return blood from the oxygenator to the vasculature of the patient.

Clause 14. The extracorporeal blood oxygenation system according to clause 13, wherein the extendable member of the infusion cannula comprises an expandable balloon, and wherein the expandable balloon is configured to expand radially outward from the sidewall of the infusion cannula.

Clause 15. The extracorporeal blood oxygenation system according to clause 13 or 14, further comprising a liquid or gas-supplying device for supplying liquid or gas to the infusion cannula, wherein the infusion cannula further comprises an inflator tube in fluid communication with the liquid or gas-supplying device and with the expandable balloon, the inflator tube extending along at least a portion of the sidewall; and wherein the inflator tube is configured to supply the liquid or gas to the expandable balloon to cause expansion of the expandable balloon.

Clause 16. The extracorporeal blood oxygenation system according to any of clauses 13 to 15, wherein the liquid or gas-supplying device is at least one of a syringe and an air pump.

Clause 17. The extracorporeal blood oxygenation system according to any of clauses 13 to 16, wherein the infusion cannula further comprises an absorbent material at least partially filling the expandable balloon, wherein the absorbent material is configured to absorb water from an environment surrounding the expandable balloon to cause expansion of the expandable balloon.

Clause 18. The extracorporeal blood oxygenation system according to any of clauses 13 to 17, wherein the absorbent material comprises a salt.

Clause 19. The extracorporeal blood oxygenation system according to any of clauses 13 to 18, wherein the expandable balloon comprises a semipermeable membrane.

Clause 20. A method of extracorporeal blood oxygenation comprising: inserting a drainage cannula into a first site of a vasculature of a patient; inserting an infusion cannula into a second site of the vasculature of the patient, the infusion cannula comprising: a main tube having a proximal end, a distal end, and a tubular sidewall extending between the proximal end and the distal end; and an extendable member provided on a portion of the sidewall, wherein the sidewall defines an aperture located between the proximal end and the distal end of the main tube; extending the extendable member of the infusion cannula radially outward from the sidewall of the infusion cannula, draining blood through the drainage cannula to a blood pump; pumping, via the blood pump, drained blood through an oxygenator to oxygenate the drained blood; and returning oxygenated blood to the vasculature of the patient via the infusion cannula.

Further details and advantages of the present disclosure will be understood from the following detailed description read in conjunction with the accompanying drawings.

DETAILED DESCRIPTION

For purposes of the description hereinafter, the terms "end," "upper," "lower," "right," "left," "vertical," "horizontal," "top," "bottom," "lateral," "longitudinal," and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments or aspects. Hence, specific dimensions and other physical characteristics related to the embodiments or aspects disclosed herein are not to be considered as limiting.

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

When used in relation to a cannula, catheter, or other device inserted into a patient, the term "proximal" refers to a portion of such device farther from the end of the device inserted into the patient. When used in relation to a cannula, catheter, or other device inserted into a patient, the term "distal" refers to a portion of such device nearer to the end of the device inserted into the patient.

Referring to the drawings, in which like reference characters refer to like parts throughout the several views thereof, various embodiments of a cannula 10 are shown. The cannula 10 is particularly suitable for insertion into a patient's vasculature for use as an infusion cannula for returning blood to the patient during a medical procedure. An example of such a medical procedure is VA ECMO of the patient's heart, in which blood is drained from the heart, circulated through an oxygenator, and returned to the patient's vasculature via the cannula 10. It is to be understood, however, that use of the cannula 10 of the present disclosure is not limited to any particular medical procedure, and reference herein to any particular use is provided only for the purpose of illustrating the various components of the cannula 10.

Figure 1:
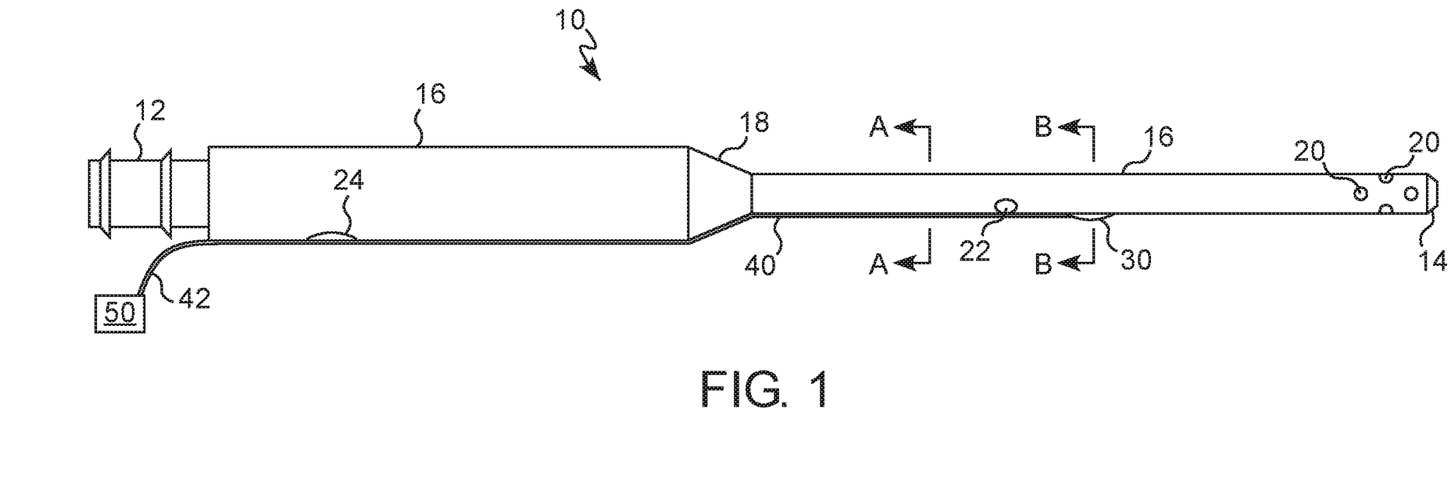
FIG. 1 is a side view of a cannula according to an embodiment of the present disclosure.

Referring now to FIG. 1, the cannula 10 includes a tube having a proximal end 12 configured for connection to a hose, tube, or other medical device. For example, the proximal end 12 may be barbed or may include a luer connector. The tube of the cannula 10 further includes a distal end 14 opposite the proximal end 12. The distal end 14 is configured for insertion into the vasculature of the patient. A tubular sidewall 16 extends between the proximal end 12 and the distal end 14 and defines a main lumen 17 (see FIG. 5) extending at least a portion of the length of the cannula 10. The sidewall 16 may be a hollow, open-ended structure allowing fluid flow into and out of the proximal end 12 and the distal end 14 via the main lumen 17. The sidewall 16 may include a tapered section 18 at which a diameter of the sidewall 16 changes. In particular, a proximal portion of the sidewall 16 between the proximal end 12 and the tapered section 18 may have a greater diameter than a distal portion of the sidewall 16 between the distal end 14 and the tapered section 18. The sidewall 16 may be formed from a flexible material such as polyurethane, polyvinyl chloride (PVC), or silicone, and may be dip molded, extruded, co-molded, or made using any other suitable manufacturing technique. In some embodiments, the sidewall 16 may be reinforced with a metal coil or mesh embedded in the sidewall 16.

With continued reference to FIG. 1, the distal end 14 of the cannula 10 may define one or more apertures 20 providing fluid communication with the main lumen 17 of the cannula 10 defined by the sidewall 16. In some embodiments, a plurality of apertures 20 may be arranged in a circular pattern extending around the outer circumference of the sidewall 16. In other embodiments, the plurality of apertures 20 may be arranged in groups disposed at various sites along the length of the sidewall 14.

With continued reference to FIG. 1, the sidewall 16 of the cannula 10 may define an auxiliary aperture 22 located between the proximal end 12 and the distal end 14 of the tube, more particularly, proximally relative to the one or more apertures 20. The auxiliary aperture 22 provides fluid communication between the main lumen 17 of the cannula 10 and the environment outside of the cannula 10.

Figure 2:
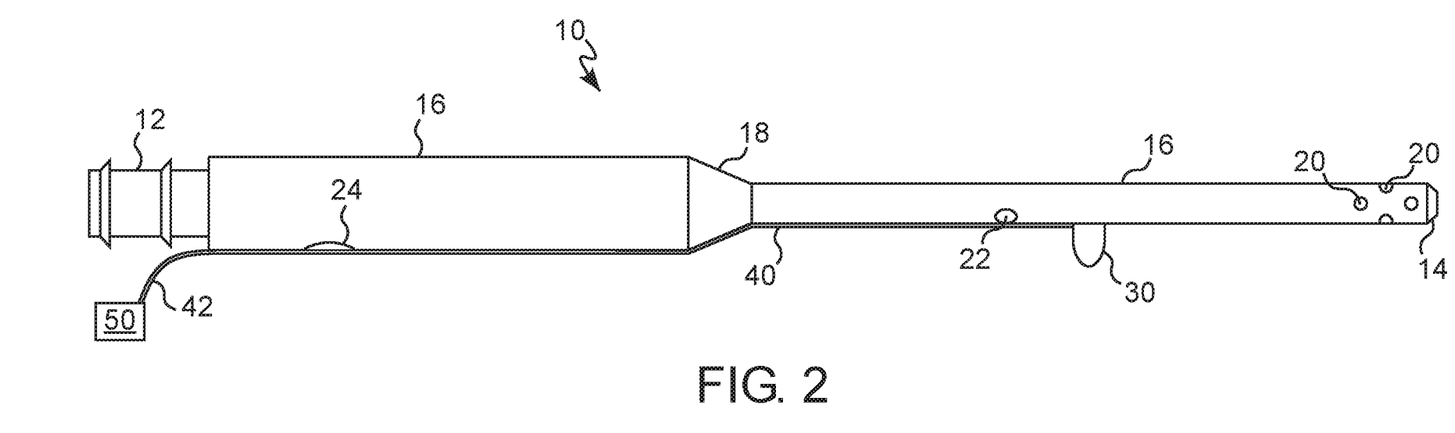
FIG. 2 is a side view of the cannula of FIG. 1, with a balloon thereof expanded.

With continued reference to FIG. 1 and further reference to FIG. 2, the cannula 10 may include an extendable member disposed on or integrally formed with the sidewall 16. In the embodiment of FIGS. 1 and 2, the extendable member is a balloon 30. The balloon 30, or other extendable member, is located between the proximal end 12 and the distal end 14 of the tube, in particular near or in the vicinity of the auxiliary aperture 22. More particularly, the balloon 30 may be located between the distal end 14 of the cannula 10 and the auxiliary aperture 22. In some embodiments, the balloon 30 may be longitudinally aligned with the auxiliary aperture 22. In some embodiments, the balloon 30 may be circumferentially aligned with the auxiliary aperture 22. In some embodiments, the one balloon 30 may be provided on a first side, either longitudinally or circumferentially, of the auxiliary aperture 22 and a second balloon 30 may be provided on a second side, either longitudinally or circumferentially, of the auxiliary aperture 22.

The balloon 30 is configured to expand radially outward from the sidewall 16 from a relaxed state, as shown in FIG. 1, to an inflated state, as shown in FIG. 2. In some embodiments, the cannula 10 may include a tube 40 in fluid communication with the balloon 30 and extending along at least a portion of the sidewall 16 toward the proximal end 12 of the cannula 10. A proximal end 42 of the tube 40 may be configured for connection to a liquid or gas-supplying device 50 for supplying liquid or gas, such as air, helium, or saline, to the tube 40 and ultimately to the balloon 30. The liquid or gas supplying device 50 is accessible to a physician or user from outside the patient when the cannula is inserted into the patient's artery or vein 80 (see FIGS. 3 and 4). Suitable liquid or gas-supplying devices 50 may include, for example, an air pump or a syringe. Liquid or gas supplied to the balloon 30 via the tube 40 causes the balloon 30 to assume the inflated state shown in FIG. 2.

The cannula 10 may further include an indicator 24 provided on a portion of the sidewall 16 that remains outside of the patient when the cannula 10 is inserted into the patient. The indicator 24 may be a printed, embedded, or embossed symbol or indicia that provides visual and/or tactile feedback to the physician or user of the orientation of the cannula 10 within the patient. For example, the indicator 24 may be provided on the same side of the sidewall 16 as the balloon 30 (or other expandable member) so that the physician or user can ascertain the relative position of the balloon 30 from the position of the indicator 24 while the balloon 30 is inside the patient and thus obscured from view. In some embodiments, the balloon 30 (or other expandable member) may be formed of a radiopaque material such that the position of the balloon 30 can be visualized while inside the patient using an x-ray, fluoroscopy, or other imaging procedure. In other embodiments, the indicator 24 may be located on a portion of the sidewall 16 that is to be inserted into the patient, and the indicator 24 may be formed of a radiopaque material such that the position of the indicator 24, and hence the position of the balloon 30, can be visualized while inside the patient using an x-ray, fluoroscopy, or other imaging procedure.

Figure 3:
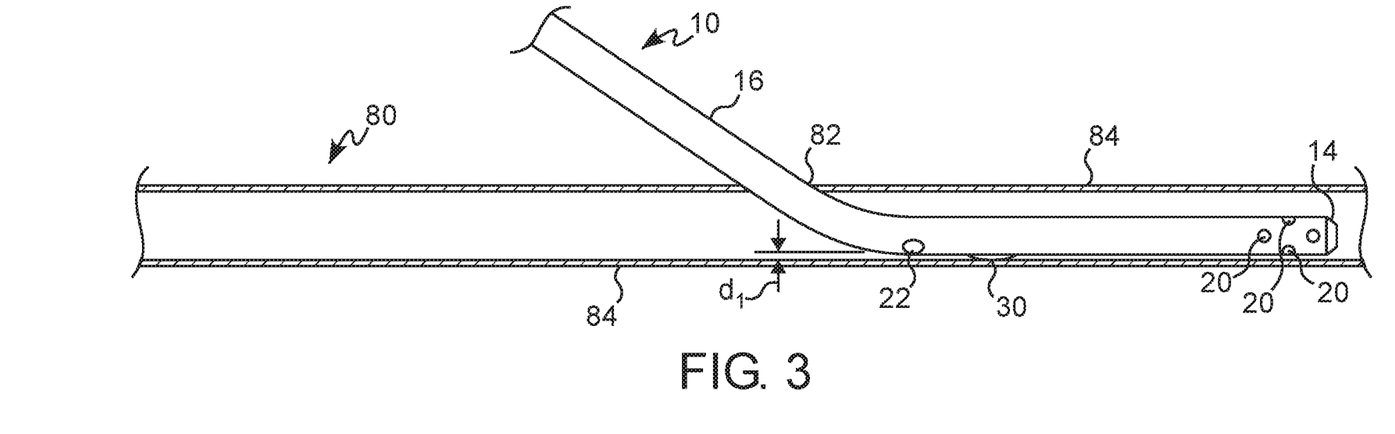
FIG. 3 is a side view of the cannula of FIG. 1 inserted into an artery or vein.
Figure 4:
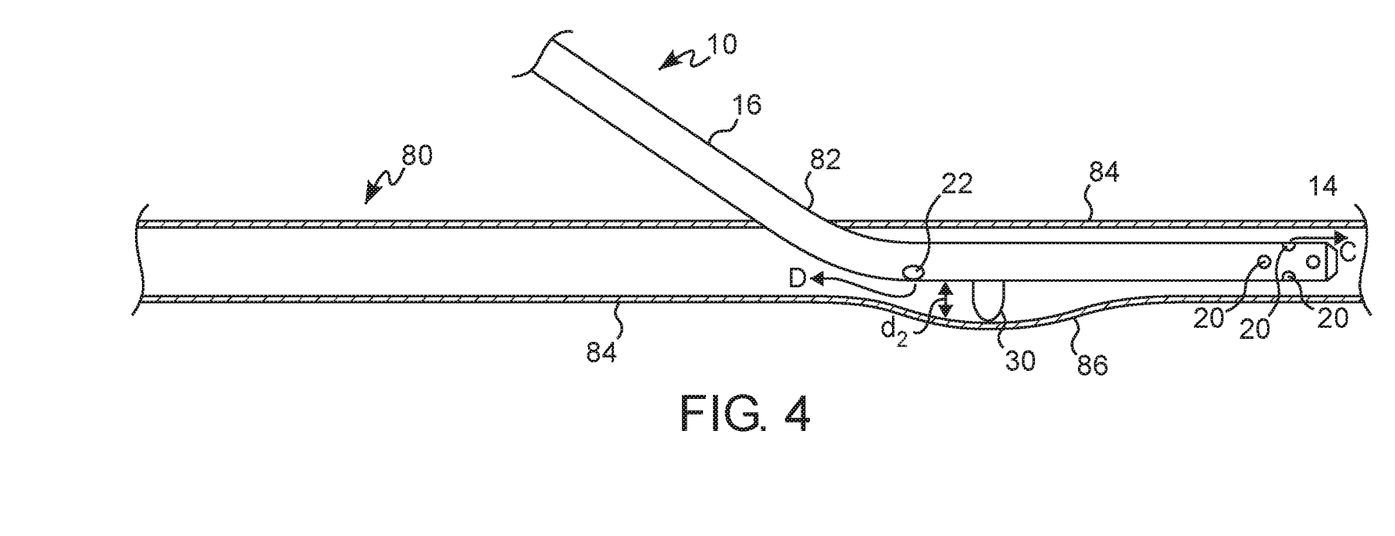
FIG. 4 is a side view of the cannula of FIG. 1 inserted into the artery or vein, with the balloon thereof expanded.

Referring now to FIGS. 3 and 4, the cannula 10 is shown inserted into an artery or vein 80 of the patient, for example the femoral artery, axial artery, or subclavian artery, for use during a medical procedure such as VA ECMO. The cannula 10 may be inserted into the artery or vein 80 such that the distal end 14 is directed toward the patient's heart in the direction of blood flow through the artery or vein 80. The cannula 10 may be inserted into the artery or vein 80 through an access location 82 in a vessel wall 84 of the artery or vein 80. In particular, the cannula 10 may be inserted into the artery or vein 80 in a percutaneous procedure using an introducer, such as a guidewire. Such a percutaneous procedure suitable for inserting the cannula 10 is described in U.S. Pat. No. 8,550,973 and U.S. Patent Application Publication No. 2018/0228960, the disclosures of which are hereby incorporated by reference in their entireties. The cannula 10 is initially inserted into the artery or vein 80 with the balloon 30 in the relaxed state, as shown in FIG. 3, to minimize the size of the access location 82 in the vessel wall 84 necessary for insertion of the cannula 10. With the balloon 30 in the relaxed state, a portion of the sidewall 16 adjacent to the auxiliary aperture 22 may be located a first distance d1 from the vessel wall 84.

Once the cannula 10 is positioned as desired within the artery or vein 80, the balloon 30 may be expanded to the inflated state, as shown in FIG. 4. As described herein with reference to FIGS. 1 and 2, the balloon 30 may be expanded by supplying a liquid or gas, such as air, helium, or saline, to the balloon 30 via the tube 40 (not shown in FIGS. 3 and 4 for clarity). Expansion of the balloon 30 may force the cannula 10 away from the vessel wall 84 and/or may deflect a section 86 of the vessel wall 84 adjacent to the balloon 30 away from the cannula 10. As such, a portion of the sidewall 16 adjacent to the auxiliary aperture 22 may be located a second distance d2 from the vessel wall 84, the second distance d2 being greater than the first distance d1. With the auxiliary aperture 22 spaced apart from the vessel wall 84 in this manner, blood and/or other fluids may flow out of the auxiliary aperture 22 unobstructed by the vessel wall 84.

With continued reference to FIG. 4, during a medical procedure, the cannula 10 may be used as an infusion cannula with the artery or vein 80 being the patient's femoral artery, axial artery, or subclavian artery. Oxygenated blood may be supplied to the cannula 10 from an extracorporeal blood pump and oxygenator, as will be described in greater detail herein with reference to FIG. 13. A portion of the oxygenated blood may flow out of the distal end 14 of the cannula in the direction of arrow C toward the patient's heart. The remainder of the oxygenated blood may flow out of the auxiliary aperture 22 in the direction of arrow D, through the space between the cannula 10 and the vessel wall 84 provided by expansion of the balloon 30. Blood flow in the direction of arrow D may be towards the patient's feet to mitigate the risk of ischemia in the patient's lower extremities.

Figure 5:
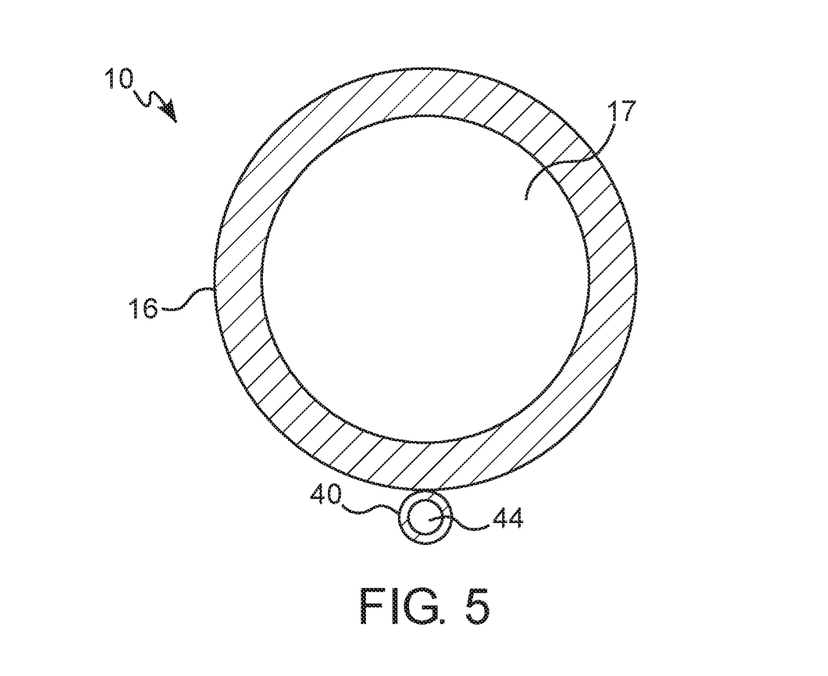
FIG. 5 is a cross-sectional view of the cannula taken along line A-A of FIG. 1.
Figure 6:
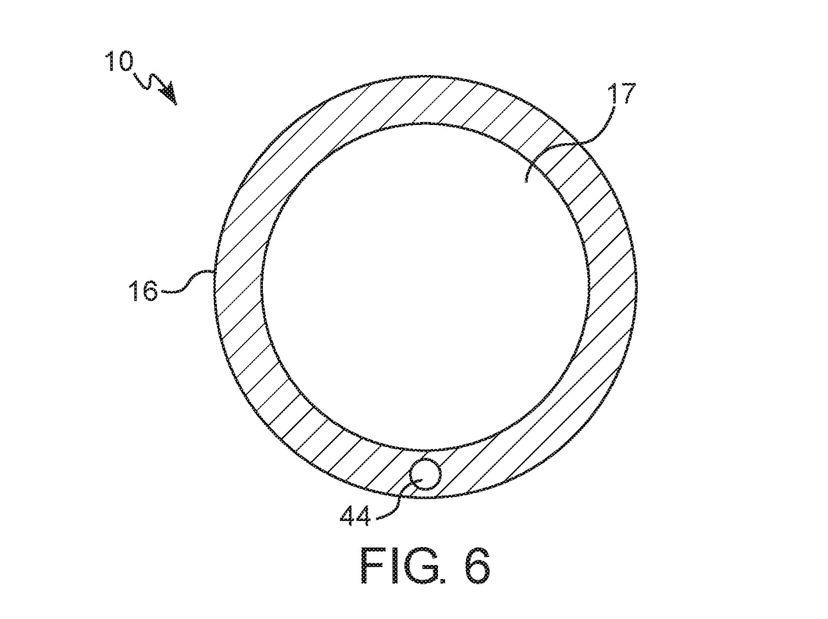
FIG. 6 is a cross-sectional view of the cannula taken along line A-A of FIG. 1, according to another embodiment of the present disclosure.

Referring now to FIG. 5, a cross-section of the cannula 10 along line A-A of FIG. 1 is shown, including the sidewall 16 and the tube 40. As described above, the sidewall 16 may define a main lumen 17 through which blood and/or other fluids may flow into and out of the cannula 10. The sidewall 16 and the main lumen 17 are shown in the accompanying drawings as having a circular structure. However, it is to be understood that the sidewall 16 and the main lumen 17 may have any cross-sectional shape such as round, curved, or polygonal that is suitable for clinical use. The tube 40 may be affixed to an outer surface of the sidewall 16 and may define a central lumen 44 through which a liquid or gas, such as air, helium, or saline, may flow into the balloon 30. The tube 40 may be formed, for example, in a co-molding or over-molding process with the sidewall 16. In another embodiment shown in FIG. 6, the central lumen 44 may be defined directly in the sidewall of the cannula 10. In still other embodiments, the tube 40 may be at least partially embedded in the sidewall 16. The tube 40 and the central lumen 44 are shown in the accompanying drawings as having a circular structure. However, it is to be understood that the tube 40 and the central lumen 44 may have any cross-sectional shape such as round, curved, or polygonal that is suitable for clinical use.

Figure 7:
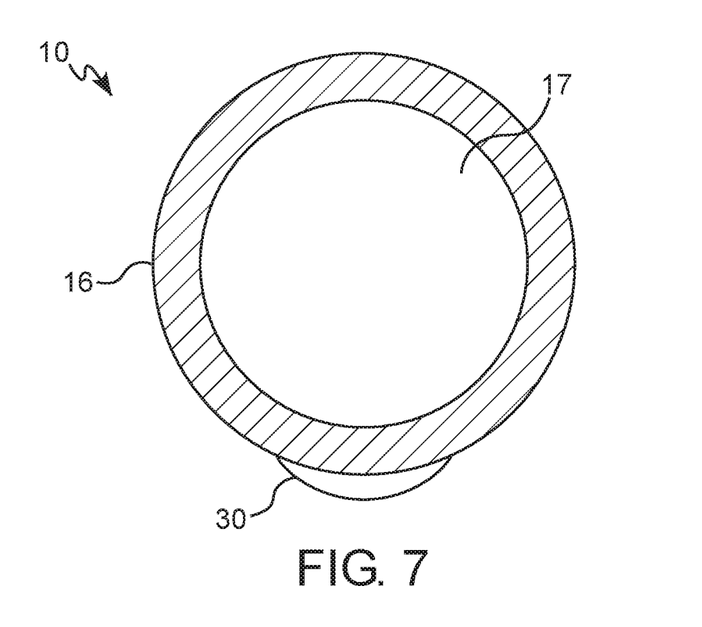
FIG. 7 is a cross-sectional view of the cannula taken along line B-B of FIG. 1.
Figure 8:
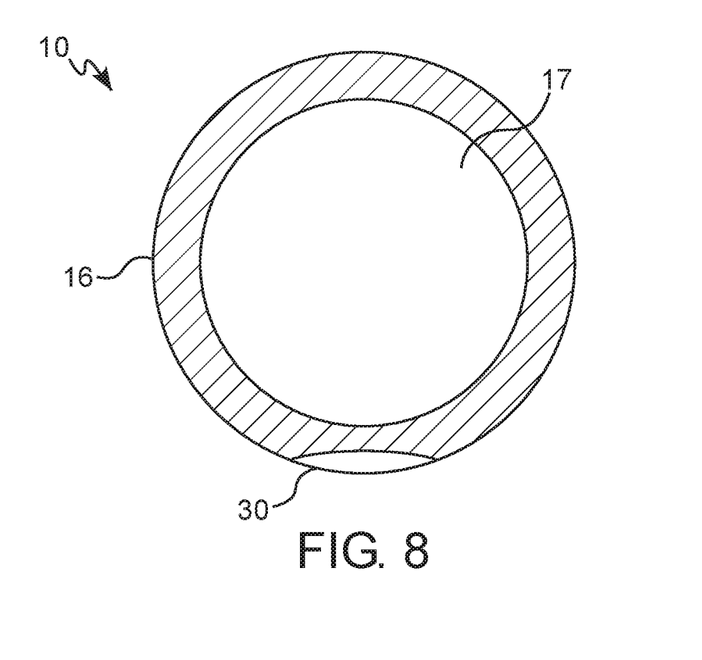
FIG. 8 is a cross-sectional view of the cannula taken along line B-B of FIG. 1, according to another embodiment of the present disclosure.

Referring now to FIGS. 7 and 8, a cross-section of the cannula 10 along line B-B of FIG. 1 is shown, including the sidewall 16 and the balloon 30. Both FIGS. 7 and 8 show the balloon 30 in the relaxed state. In the embodiment shown in FIG. 7, the balloon 30 is disposed on the outer surface of the sidewall 16. In the embodiment shown in FIG. 8, the balloon 30 is at least partially recessed into the sidewall 16 such that the balloon 30 is substantially flush with the outer surface of the sidewall 16 in the relaxed state. In some embodiments, the balloon 30 may be formed of a material different than the material of the sidewall 16. In some embodiments, the balloon 30 may be formed of a compliant material, such as latex or polyurethane, which can stretch as liquid or gas is supplied to the balloon 30. In some embodiments, the balloon 30 may be formed of a non-compliant material, such as nylon or polyethylene terephthalate (PET), which cannot appreciably stretch and therefore limits the size of the balloon 30 in the inflated state.

With continued reference to FIGS. 7 and 8, the balloon 30 may extend only partially around the circumference of the sidewall such that, in the inflated state (see, e.g., FIG. 4), fluid in the artery or vein 80 may flow freely around the balloon 30. In other embodiments, the balloon 30 may extend around the entire circumference of the sidewall 16 such that, in the inflated state, the balloon 30 forms a barrier in the artery or vein 80 substantially prohibiting fluid flow between a section of the artery or vein 80 upstream of the balloon 30 and a section of the artery or vein 80 downstream of the balloon.

Figure 9:
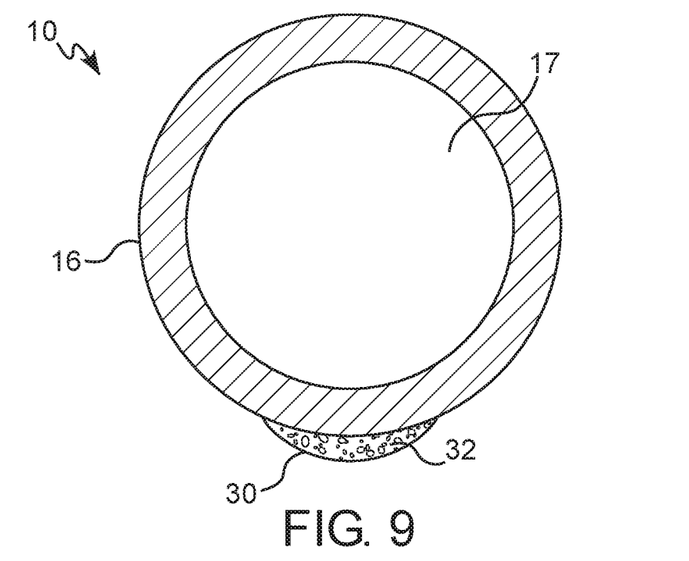
FIG. 9 is a cross-sectional view of the cannula taken along line B-B of FIG. 1, according to another embodiment of the present disclosure.
Figure 10:
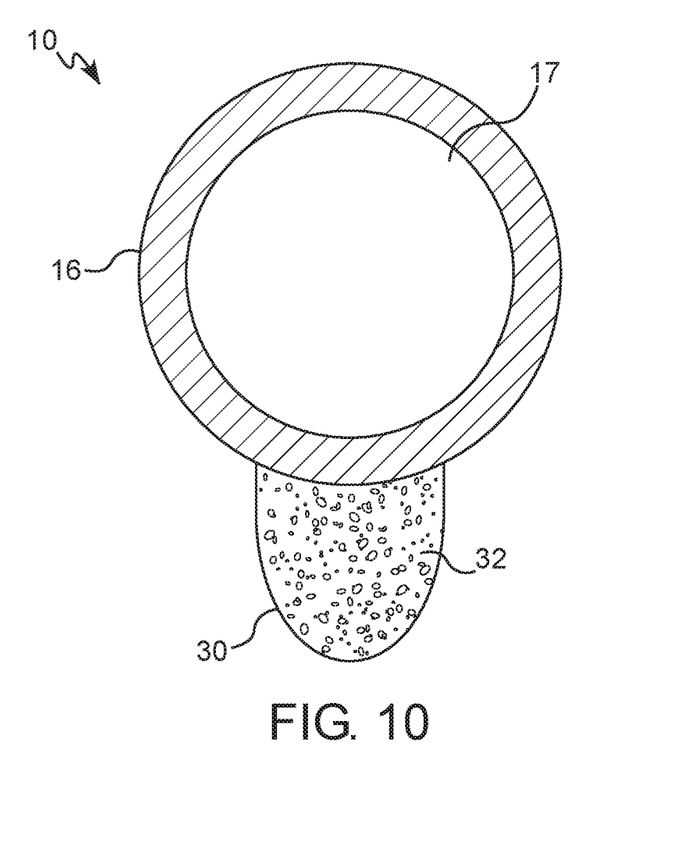
FIG. 10 is a cross-sectional view of the cannula of FIG. 9, with the balloon thereof expanded.

Referring now to FIGS. 9 and 10, in some embodiments, the balloon 30 may be formed of a semipermeable membrane, and the balloon 30 may be at least partially filled or packed with an absorbent material 32. The absorbent material 32 is selected to be a material which expands upon absorbing water from a surrounding environment. Examples of suitable absorbent materials 32 may include various salts. FIG. 9 shows the balloon in the relaxed state, prior to insertion into the patient. Upon insertion into the vasculature of the patient, water from the patient's blood is absorbed by the absorbent material 32 through the semipermeable membrane of the balloon 30, causing the balloon to expand to the inflated state shown in FIG. 10. Because the absorbent material 32 passively inflates the balloon 30 upon insertion into the patient, the tube 40 and the liquid or gas-supplying device 50 are not required and may be omitted in the embodiment of FIGS. 9 and 10.

Figure 11:
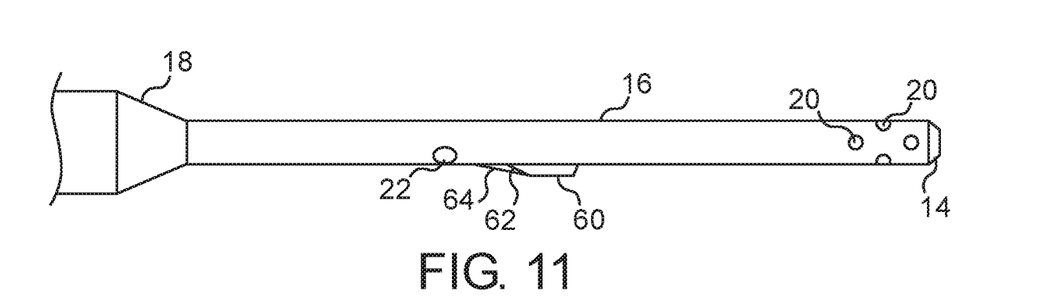
FIG. 11 is a side view of a cannula according to another embodiment of the present disclosure.
Figure 12:
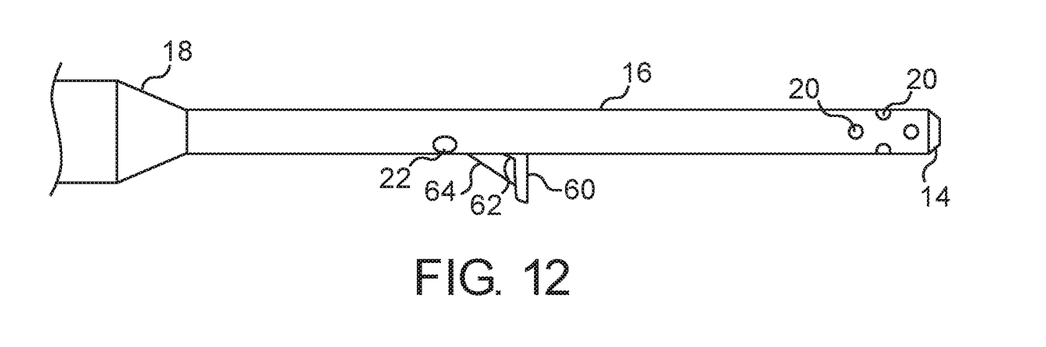
FIG. 12 is a side view of the cannula of FIG. 11, with a flap thereof extended.

Referring now to FIGS. 11 and 12, in other embodiments, the extendable member of the cannula 10 may be a flap 60 pivotally connected to the sidewall 16 via a hinge 62. The flap may be moveable between a retracted position, shown in FIG. 11, and an extended position shown in FIG. 12. In the retracted position, the flap 60 extends substantially parallel to the sidewall 16 to minimize the cross-sectional area of the cannula 10. In the extended position, the flap 60 extends radially outward from the sidewall 16 at an angle of, for example, approximately 90°. The flap 60 may be rotated about the hinge 62 between the retracted position and the extended position by a mechanical actuator 64, such as a cable or spring, which can be accessed by the physician or user from outside the patient when the cannula is inserted into the patient's artery or vein 80. The flap 60 provides similar functionality to the balloon 30 of the embodiments of FIGS. 1-10. In particular, movement of the flap 60 to the extended position may force the cannula 10 away from the vessel wall 84 and/or may deflect a section 86 of the vessel wall 84 adjacent to the flap 60 away from the cannula 10. As such, the auxiliary aperture 22 is spaced apart from the vessel wall 84 to ensure blood and/or other fluids may flow out of the auxiliary aperture 22 unobstructed by the vessel wall 84. In some embodiments, the flap 60 may be formed of the same material as the sidewall 16 and the hinge 62 may be a living hinge. In some embodiments, the flap 60 may have a rigid material, such as a metal, embedded therein to provide stiffness and resistance to deformation. In some embodiments, the flap 60 and/or the hinge 62 may be composed of a temperature sensitive material such that the flap 60 rests in the retracted position when the cannula 10 is stored outside the patient at ambient temperature, but the flap 60 automatically rotates to the extended position when inserted into the patient and exposed to the body temperature of the patient. In some embodiments the hinge 62 may operate electromechanically and be activated by button press outside the device.

Figure 13:
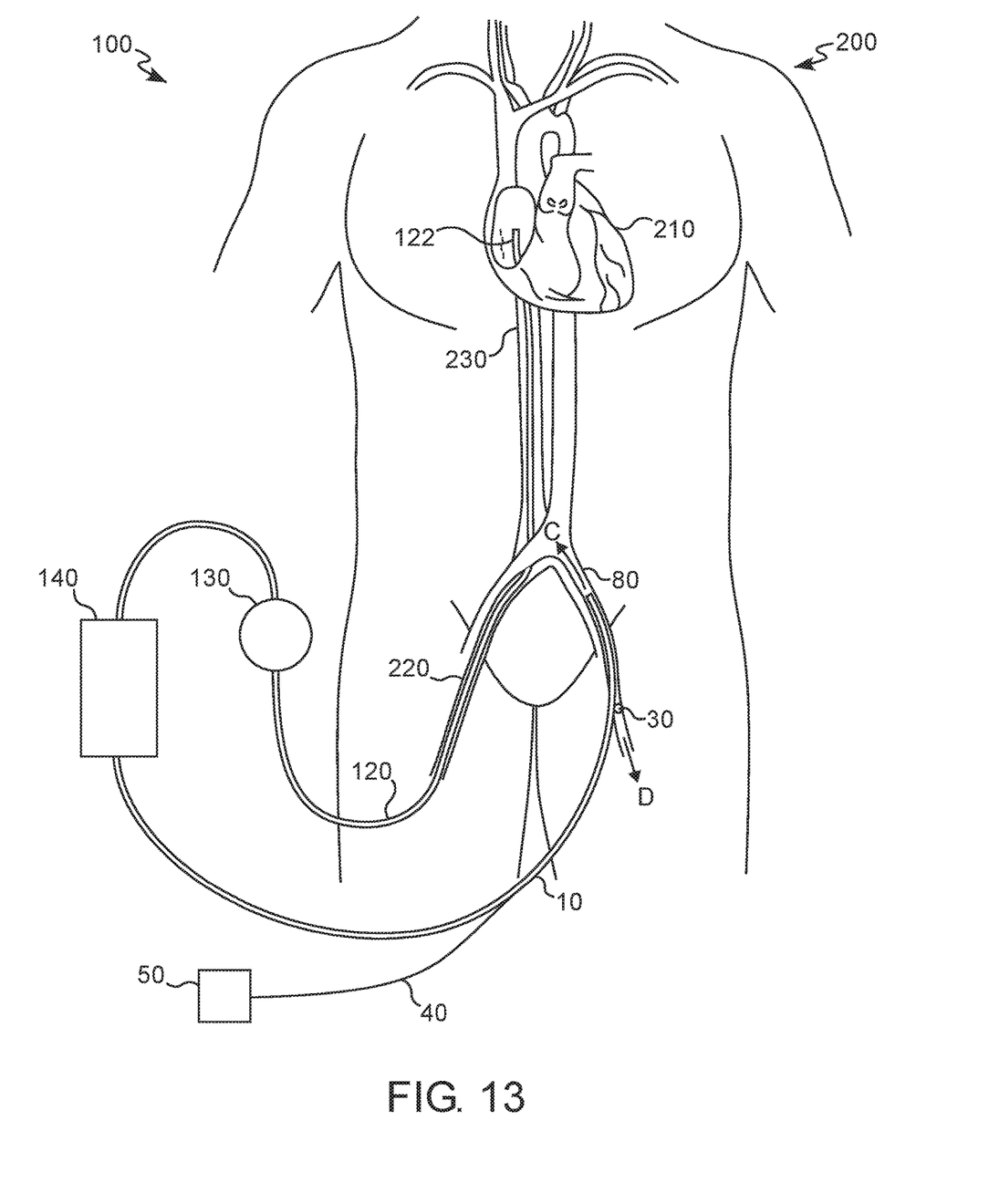
FIG. 13 is a schematic diagram of an extracorporeal blood oxygenation system including a cannula according to an embodiment of the present disclosure.

Referring now to FIG. 13, an extracorporeal blood oxygenation system 100, for example a VA ECMO system, in which the cannula 10 is used as an infusion cannula is shown schematically in use on a patient 200. In general, the extracorporeal blood oxygenation system 100 drains unoxygenated blood from the patient 200, pumps the unoxygenated blood through an oxygenator 140, and returns oxygenated blood to the patient 200. The extracorporeal blood oxygenation system 100 includes a drainage cannula 120 which may be inserted into the vasculature of the patient 200. For example, the drainage cannula 120 may be inserted in the femoral vein 220 of the patient 200 and guided up the inferior vena cava 230. A distal end 122 of the drainage cannula 120 may thus be positioned in the vicinity of the junction of the inferior vena cava 230, the superior vena cava, and the right atrium of the patient's heart 210. A portion of the drainage cannula 120 remains outside the body of the patient 200 and is fluidly connected to a blood pump 130, which in turn is fluidly connected to the oxygenator 140. The oxygenator 140 is fluidly connected to the cannula 10, which may be positioned in the artery or vein 80 of the patient 200, for example the femoral artery, as described herein with reference to FIGS. 3 and 4. In particular, a portion of the cannula 10 may be inserted into the artery or vein 80, and the balloon 30 of the cannula may be expanded by actuating the liquid or gas-supplying device to supply liquid or gas to the balloon 30 via the line 40. It is to be understood that while FIG. 13 illustrates one arrangement of the extracorporeal blood oxygenation system 100, the infusion cannula 10 and the drainage cannula 120 may be positioned in other portions of the patient's vasculature for various clinical reasons. For example, the drainage cannula 120 may be positioned in the jugular vein of the patient 200, or the system 100 may include two drainage cannula 120 respectively inserted into the femoral vein 220 and the jugular vein.

In use, the pump 130 draws unoxygenated blood from the patient's heart 210 into the drainage cannula 120 and out of the patient 200. The pump 130 then forces the unoxygenated blood through the oxygenator 140, which oxygenates the blood in preparation for returning the blood to the patient 200. The oxygenated blood leaving the oxygenator 140 is then forced by the pump 130 into the cannula 10 and ultimately is returned to the artery or vein 80 of the patient 200. A portion of the blood returned to the artery or vein 80 by the cannula 10 may be directed out of the distal end 14 (see FIGS. 1-4) of the cannula 10 toward the patient's heart 210 in the direction of arrow C, while a remainder of the blood returned to the artery or vein 80 by the cannula 10 may be directed out of the auxiliary aperture 22 (see FIGS. 1-4) toward the patient's feet in the direction of arrow D. Further details of the various components and processes of the extracorporeal blood oxygenation system 100 are described in U.S. Pat. No. 8,550,973 and U.S. Patent Application Publication No. 2018/0228960, the disclosures of which are hereby incorporated by reference in their entireties. For example, the pump 130 can be any centrifugal, axial, mixed, or roller pump that can produce adequate flowrates through the system. Several examples of pumps include, without limitation the TANDEMHEART pump manufactured by CardiacAssist, Inc., the BIOMEDICUS pump manufactured by Medtronic, Inc., the ROTAFLOW pump manufactured by Jostra Medizintechnik AG, the CENTRIMAG pump manufactured by Levitronix, LLC, the SARNS DELPHIN pump manufactured by the Terumo Cardiovascular Group, the REVOLUTION pump manufactured by Cobe Cardiovascular, Inc., and others.

While several embodiments of a drainage cannula are shown in the accompanying figures and described hereinabove in detail, other embodiments will be apparent to, and readily made by, those skilled in the art without departing from the scope and spirit of the invention. For example, it is to be understood that this disclosure contemplates, to the extent possible, that one or more features of any embodiment can be combined with one or more features of any other embodiment. Accordingly, the foregoing description is intended to be illustrative rather than restrictive.

What is claimed is:

1. A cannula comprising:
   a main tube having a proximal end, a distal end, and a tubular sidewall extending between the proximal end and the distal end; and
   an expandable balloon provided on a portion of the sidewall, wherein the expandable balloon is configured to expand radially outward from the sidewall;
   wherein the sidewall defines an aperture located between the proximal end and the distal end of the main tube;
   wherein an exterior surface of the sidewall of the main tube is exposed from a proximalmost end of the expandable balloon to a distalmost end of the expandable balloon.

2. The cannula according to claim 1, further comprising an inflator tube in fluid communication with the expandable balloon and extending along at least a portion of the sidewall,
   wherein the inflator tube is configured to supply liquid or gas to the expandable balloon to cause expansion of the expandable balloon.

3. The cannula according to claim 2, wherein the liquid or gas supplied by the inflator tube is at least one of air, helium, and saline.

4. The cannula according to claim 1, further comprising a lumen defined in the sidewall and in fluid communication with the expandable balloon,
   wherein the lumen is configured to supply liquid or gas to the expandable balloon to cause expansion of the expandable balloon.

5. The cannula according to claim 1, wherein the expandable balloon comprises at least one of a compliant material and a noncompliant material.

6. The cannula according to claim 1, further comprising an absorbent material at least partially filling the expandable balloon,
   wherein the absorbent material is configured to absorb water from an environment surrounding the expandable balloon to cause expansion of the expandable balloon.

7. The cannula according to claim 6, wherein the absorbent material comprises a salt.

8. The cannula according to claim 6, wherein the expandable balloon comprises a semipermeable membrane.

9. A cannula comprising:
   a main tube having a proximal end, a distal end, and a tubular sidewall extending between the proximal end and the distal end;
   an extendable member provided on a portion of the sidewall, wherein the extendable member comprises a flap pivotally connected to the sidewall via a hinge; and
   a mechanical actuator configured to rotate the flap about the hinge between the retracted position and the extended position;
   wherein the extendable member is configured to extend radially outward from the sidewall;
   wherein the sidewall defines an aperture located between the proximal end of the main tube and the distal end of the main tube;
   wherein the flap is configured to rotate about the hinge between a retracted position in which the flap extends substantially parallel to the sidewall and an extended position in which the flap extends radially outward from the sidewall;
   wherein the flap comprises a temperature sensitive material and is configured to rotate to the extended position upon exposure to a body temperature of the patient.

10. An extracorporeal blood oxygenation system comprising:
    a drainage cannula configured for insertion into a vasculature of a patient;
    a blood pump fluidly connected to the drainage cannula and configured to draw blood from the patient via the drainage cannula;
    an oxygenator in fluid communication with the blood pump and configured to receive blood from the blood pump;
    an infusion cannula configured for insertion into the vasculature of the patient, the infusion cannula comprising:

a main tube having a proximal end, a distal end, and a tubular sidewall extending between the proximal end and the distal end; and an expandable balloon, wherein an entirety of the expandable balloon extends only partially around a circumference of the sidewall, the circumference lying in a plane perpendicular to a central longitudinal axis of the main tube, wherein the expandable balloon is configured to extend radially outward from the sidewall, wherein the sidewall defines an aperture located between the proximal end and the distal end of the main tube, wherein a proximal end of the infusion cannula is in fluid communication with the oxygenator and configured to return blood from the oxygenator to the vasculature of the patient.

11. The extracorporeal blood oxygenation system according to claim 10, further comprising a liquid or gas-supplying device for supplying liquid or gas to the infusion cannula, wherein the infusion cannula further comprises an inflator tube in fluid communication with the liquid or gas-supplying device and with the expandable balloon, the inflator tube extending along at least a portion of the sidewall; and wherein the inflator tube is configured to supply the liquid or gas to the expandable balloon to cause expansion of the expandable balloon.

12. The extracorporeal blood oxygenation system according to claim 11, wherein the liquid or gas-supplying device is at least one of a syringe and an air pump.

13. The extracorporeal blood oxygenation system according to claim 10, wherein the infusion cannula further comprises an absorbent material at least partially filling the expandable balloon, wherein the absorbent material is configured to absorb water from an environment surrounding the expandable balloon to cause expansion of the expandable balloon.

14. The extracorporeal blood oxygenation system according to claim 13, wherein the absorbent material comprises a salt.

15. The extracorporeal blood oxygenation system according to claim 13, wherein the expandable balloon comprises a semipermeable membrane.

16. A method of extracorporeal blood oxygenation comprising:

inserting a drainage cannula into a first site of a vasculature of a patient;

inserting an infusion cannula into a second site of the vasculature of the patient, the infusion cannula comprising:

a main tube having a proximal end, a distal end, and a tubular sidewall extending between the proximal end and the distal end; and an extendable member provided on a portion of the sidewall, wherein the extendable member defines an exposed outer surface of the sidewall extending from a proximal end of the extendable member and a distal end of the extendable member;

wherein the sidewall defines an aperture located between the proximal end and the distal end of the main tube;

extending the extendable member of the infusion cannula radially outward from the sidewall of the infusion cannula to engage an inner wall of the vasculature of the patient;

wherein when the extendable member is engaged with the inner wall of the vasculature, blood is permitted to flow from proximal of the extendable member past the extendable member along and while in contact with the exposed outer surface of the sidewall to distal of the extendable member;

draining blood through the drainage cannula to a blood pump;

pumping, via the blood pump, drained blood through an oxygenator to oxygenate the drained blood; and returning oxygenated blood to the vasculature of the patient via the infusion cannula.

17. The method of claim 16, wherein the extendable member is an inflatable balloon extending only partially around a circumference of the sidewall.

18. The method of claim 16, wherein extending the extendable member includes extending the extendable member radially outward from the sidewall only on one side of a plane containing a central longitudinal axis of the main tube.

19. The cannula of claim 9, wherein in the extended position, the flap extends generally perpendicular to a central longitudinal axis of the main tube.

20. The cannula of claim 9, wherein the flap is configured to rest in the retracted position at ambient temperature outside of the patient.

* * * * *